United States Patent
Nakajima

(10) Patent No.: US 9,776,787 B2
(45) Date of Patent: Oct. 3, 2017

(54) FOAM FORMING AEROSOL DISPENSER

(75) Inventor: Yasutomo Nakajima, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 129 days.

(21) Appl. No.: 14/348,965

(22) PCT Filed: Aug. 16, 2012

(86) PCT No.: PCT/JP2012/070787
§ 371 (c)(1),
(2), (4) Date: Apr. 1, 2014

(87) PCT Pub. No.: WO2014/027410
PCT Pub. Date: Feb. 20, 2014

(65) Prior Publication Data
US 2014/0246515 A1    Sep. 4, 2014

(51) Int. Cl.
*B65D 83/14*    (2006.01)
*B65D 83/68*    (2006.01)
(Continued)

(52) U.S. Cl.
CPC ............ *B65D 83/682* (2013.01); *A61K 8/046* (2013.01); *A61K 8/342* (2013.01); *A61K 8/36* (2013.01);
(Continued)

(58) Field of Classification Search
CPC ...... B65D 83/682; B65D 83/62; B65D 83/68; C11D 17/041; C11D 17/045; C11D 17/0043; A61K 8/046
(Continued)

(56) References Cited

U.S. PATENT DOCUMENTS 3,709,437 A * 1/1973 Wright .......................... 239/343
6,758,411 B2 * 7/2004 Conway ............... C11D 17/041
                                                              215/10
(Continued)

FOREIGN PATENT DOCUMENTS

CN          1826168 A      8/2006
JP     2000-297007 A     10/2000
(Continued)

OTHER PUBLICATIONS

International Search Report for PCT/JP2012/070787 mailed Nov. 27, 2012.
(Continued)

*Primary Examiner* — Alexander Valvis
(74) *Attorney, Agent, or Firm* — Holtz, Holtz & Volek PC

(57) ABSTRACT

A foam forming aerosol product including a double structure container having a propellant filling space, two liquid concentrate filling spaces, and a discharging mechanism for simultaneously discharging contents filled in the two liquid concentrate filling spaces. The propellant filling space is filled with a propellant containing a compressed gas. A first liquid concentrate filling space is filled with a first liquid concentrate composition containing 0.5 to 15.0% by mass of an organic acid, and a second liquid concentrate filling space is filled with a second liquid concentrate composition containing 0.5 to 15.0% by mass of a hydrogen carbonate. The first liquid concentrate composition discharged from the first liquid concentrate filling space and the second liquid concentrate composition discharged from the second liquid concentrate filling space are mixed to form a foam. The foam forming aerosol product can be safely used, has an excellent storage stability and is capable of readily forming a foam.

7 Claims, 4 Drawing Sheets

(51) Int. Cl.
  *C11D 17/00* (2006.01)
  *C11D 17/04* (2006.01)
  *B65D 83/62* (2006.01)
  *C09K 3/30* (2006.01)
  *A61K 8/34* (2006.01)
  *A61K 8/36* (2006.01)
  *A61Q 19/00* (2006.01)
  *A61K 8/04* (2006.01)

(52) U.S. Cl.
  CPC ............ *A61Q 19/00* (2013.01); *B65D 83/62* (2013.01); *B65D 83/68* (2013.01); *C09K 3/30* (2013.01); *C11D 17/0043* (2013.01); *C11D 17/041* (2013.01); *A61K 2800/10* (2013.01)

(58) Field of Classification Search
  USPC .................... 239/304, 307; 222/94, 135, 136
  See application file for complete search history.

(56) References Cited

U.S. PATENT DOCUMENTS

| | | | | |
|---|---|---|---|---|
| 7,448,556 B2 * | 11/2008 | Muehlhausen | .... | B65D 81/3283 222/129 |
| 7,798,366 B2 * | 9/2010 | Hoshino | ................ | B65D 83/62 222/105 |
| 2005/0026269 A1 * | 2/2005 | Kottwitz | .................. | C12N 9/54 435/222 |
| 2007/0140042 A1 | 6/2007 | Schanz et al. | | |
| 2007/0155843 A1 * | 7/2007 | Martel et al. | .................. | 521/50 |
| 2011/0215113 A1 * | 9/2011 | Hansen et al. | ................ | 222/136 |

FOREIGN PATENT DOCUMENTS

| | | |
|---|---|---|
| JP | 2000-297008 A | 10/2000 |
| JP | 2004-161292 A | 6/2004 |
| JP | 2006-528586 A | 12/2006 |
| JP | 2009-091365 A | 4/2009 |
| JP | 2011-1282 A | 1/2011 |

OTHER PUBLICATIONS

Chinese Office Action (and English translation thereof) dated Apr. 24, 2015, issued in counterpart Chinese Application No. 201280056033.7.

* cited by examiner

FOAM FORMING AEROSOL DISPENSER

CROSS-REFERENCE TO RELATED APPLICATION

This application is a United States national phase application of International Application PCT/JP2012/070787 filed on Aug. 16, 2012.

TECHNICAL FIELD

The present invention relates to a foam forming aerosol product.

BACKGROUND ART

One type of aerosol product that has hitherto been known is configured to hold an aerosol composition including a liquid concentrate that contains active ingredients and a propellant in an aerosol container, which is a pressure resistant container having a spraying valve. The aerosol product delivers a foamy discharge as the evaporating propellant forms bubbles in the discharged liquid.

In order to achieve favorable foam-forming ability or stability of discharged foam, a liquefied gas such as liquefied petroleum gas or dimethyl ether is used as the propellant in such a foam forming aerosol product. Since these liquefied gases are combustible, there are the problems of danger in handling them depending on the environment in which they are used, and of the possibility of explosion hazards when disposing the aerosol container. Although liquefied petroleum gas and dimethyl ether produce less airborne particulate matter or greenhouse gases as compared to other fossil fuels, they may nevertheless adversely affect the environment.

A combination of compositions, such as an organic acid composition containing an organic acid such as citric acid, for example, and a hydrogen carbonate composition containing a hydrogen carbonate such as sodium hydrogen carbonate, for example, is known to form a foam as they generate carbon dioxide gas when mixed together (see, for example, Patent Literatures 1 to 3).

However, since these compositions containing organic acid and hydrogen carbonate must be separately held in tube- or cup-shaped containers that are hermetically sealed with a lid, they need to be dispensed from the respective containers and mixed when used, which is a complicated process. Moreover, they may not be mixed in an appropriate mixing ratio because of the difficulty to adjust the amount dispensed from the respective containers. Another problem is that, the compositions in the containers are exposed to the air each time they are dispensed, which may compromise their stability over a long term storage.

CITATION LIST

Patent Literature

Patent Literature 1: Japanese Patent Application Laid-Open No. 2000-297007
Patent Literature 2: Japanese Patent Application Laid-Open No. 2000-297008
Patent Literature 3: Japanese Patent Application Laid-Open No. 2009-091365

SUMMARY OF INVENTION

Technical Problem

The present invention has been made in view of the foregoing circumstances and has its object the provision of a foam forming aerosol product that can be used highly safely irrespective of the environment in which it is used and that has excellent storage stability and is capable of readily forming a favorable foam.

Solution to Problem

The foam forming aerosol product of the present invention includes a double structure container having a propellant filling space, two independent liquid concentrate filling spaces, and a discharging mechanism for simultaneously discharging contents filled in the two liquid concentrate filling spaces, wherein:

the propellant filling space in the double structure container is filled with a propellant composed of a compressed gas;

a first liquid concentrate composition containing an organic acid, water, a surfactant, and a higher alcohol is filled in a first liquid concentrate filling space of the double structure container, the organic acid being contained in a content ratio of 0.5 to 15.0% by mass;

a second liquid concentrate composition containing a hydrogen carbonate, water, a surfactant, and a higher alcohol is filled in a second liquid concentrate filling space of the double structure container, the hydrogen carbonate being contained in a content ratio of 0.5 to 15.0% by mass; and the first liquid concentrate composition discharged from the first liquid concentrate filling space and the second liquid concentrate composition discharged from the second liquid concentrate filling space are mixed to form a foam.

In the foam forming aerosol product of the present invention, the mixture ratio of the first liquid concentrate composition discharged from the first liquid concentrate filling space and the second liquid concentrate composition discharged from the second liquid concentrate filling space (mass of the first liquid concentrate composition: mass of the second liquid concentrate composition) may preferably be 0.8:1.2 to 1.2:0.8.

In the foam forming aerosol product of the present invention, the first liquid concentrate composition may preferably have a viscosity of 10 to 15000 mPa·s at a temperature of 20° C., the second liquid concentrate composition may preferably have a viscosity of 10 to 15000 mPa·s at a temperature of 20° C., and also each of the viscosity of the first liquid concentrate composition and the viscosity of the second liquid concentrate composition may preferably fall within a range of ±20% of an average of the viscosities of the first liquid concentrate composition and the second liquid concentrate composition.

In the foam forming aerosol product of the present invention, the discharging mechanism may preferably include a mixing space for mixing the first liquid concentrate composition discharged from the first liquid concentrate filling space and the second liquid concentrate composition discharged from the second liquid concentrate filling space.

The foam forming aerosol product of the present invention may preferably be intended to be applied to the human body.

Advantageous Effects of Invention

The foam forming aerosol product of the present invention includes a double structure container having a discharging mechanism for simultaneously discharging contents filled in two liquid concentrate filling spaces, wherein a first liquid concentrate composition containing a specific ratio of an organic acid is filled in one of the two liquid concentrate filling spaces, while a second liquid concentrate composition containing a specific ratio of a hydrogen carbonate is filled in the other liquid concentrate filling space. Thus, the first liquid concentrate composition and the second liquid concentrate composition can be discharged from the respective two liquid concentrate filling spaces of the double structure container in appropriate amounts at the same time. Thus the first liquid concentrate composition and the second liquid concentrate composition are always mixed in a constant ratio, as a result of which a favorable foam is readily formed by carbon dioxide gas that is generated by the reaction between the organic acid and the hydrogen carbonate. Since an incombustible compressed gas is used as the propellant of the first liquid concentrate composition and the second liquid concentrate composition, the product can be used highly safely irrespective of the environment in which it is used. Moreover, as neither of the first liquid concentrate composition and the second liquid concentrate composition is exposed to the air outside the container when used, they can be maintained stable over a long term storage.

Accordingly, the foam forming aerosol product of the present invention can be used highly safely irrespective of the environment in which it is used, has excellent storage stability, and is capable of readily forming a favorable foam.

DESCRIPTION OF EMBODIMENTS

Figure 1:
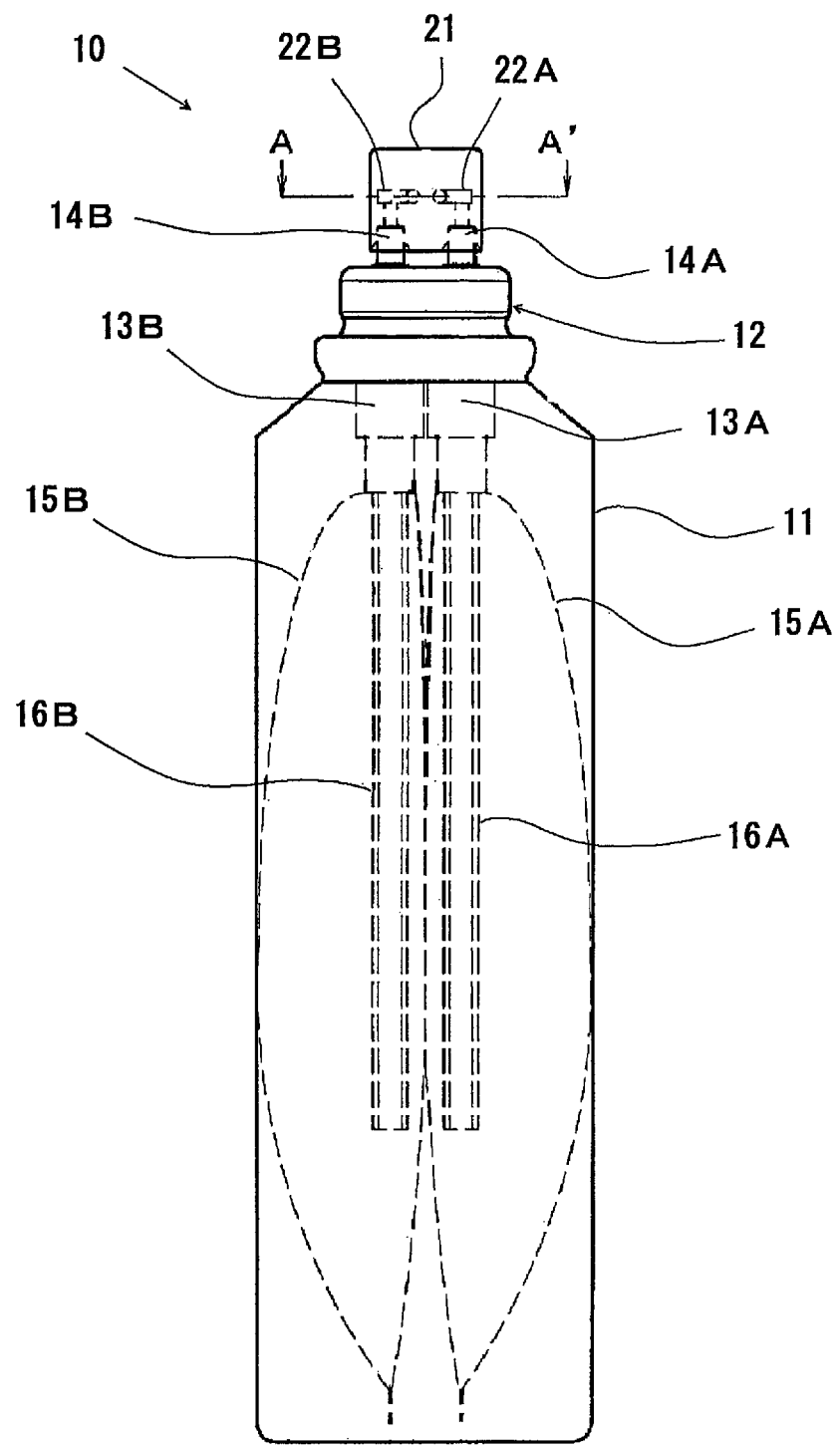
FIG. 1 is a diagram illustrating one example of the structure of the double structure container used for the foam forming aerosol product of the present invention.

The foam forming aerosol product of the present invention includes a double structure container having a propellant filling space, two independent liquid concentrate filling spaces, and a discharging mechanism for simultaneously discharging contents filled in the two liquid concentrate filling spaces. In the double structure container, the propellant filling space is filled with a propellant composed of a compressed gas, and a first liquid concentrate filling space is filled with a first liquid concentrate composition that contains an organic acid, while a second liquid concentrate filling space is filled with a second liquid concentrate composition that contains a hydrogen carbonate.

The foam forming aerosol product of the present invention forms a foam produced by means of carbon dioxide gas that is generated by the reaction between an organic acid and a hydrogen carbonate upon mixing of the first and second liquid concentrate compositions discharged simultaneously from the first and second liquid concentrate filling spaces, respectively.

First Liquid Concentrate Composition

The first liquid concentrate composition contains an organic acid, water, a surfactant, and a higher alcohol as essential components, with the organic acid being contained in a content ratio of 0.5 to 15.0% by mass.

Examples of organic acids, as an essential component of the first liquid concentrate composition, include citric acid, lactic acid, fumaric acid and tartaric acid.

These may be used either singly or in any combination thereof.

Organic acid may preferably be a citric acid from the viewpoints of its solubility to water and the ability to produce carbon dioxide.

The content ratio of the organic acid needs to be 0.5 to 15.0% by mass, and is preferably 2.0 to 10.0% by mass, more preferably 4.0 to 9.0% by mass, per 100% by mass of the first liquid concentrate composition.

If the content ratio of the organic acid is too high, the organic acid may not be fully dissolved in the first liquid concentrate composition, or the viscosity of the first liquid concentrate composition may decrease, which may lead to dripping at the site of application. The production cost will be higher, too. On the other hand, if the content ratio of the organic acid is too low, sufficient foam-forming ability cannot be achieved.

Water as an essential component of the first liquid concentrate composition may be purified water or ion-exchanged water.

The content ratio of water is preferably 70.0 to 99.0% by mass, more preferably 75.0 to 95.0% by mass, particularly preferably 80.0 to 90.0% by mass, per 100% by mass of the first liquid concentrate composition.

If the content ratio of water is too high, other ingredients may not be contained in a sufficient ratio. On the other hand, if the content ratio of water is too low, sufficient foam-forming ability may not be achieved, and the production cost may be increased.

As a surfactant, which is an essential component of the first liquid concentrate composition, a nonionic surfactant may preferably be used, as it is hardly affected by an organic acid.

Examples of the nonionic surfactants that are preferable from the viewpoint of foam-forming ability include those having an HLB value of 10 to 18 including polyoxyethylene sorbitan fatty acid ester, polyoxyethylene sorbitol fatty acid ester, polyoxyethylene hardened castor oil, polyoxyethylene sterol/hydrogenated sterol, polyoxyethylene alkyl ether, polyoxyethylene polyoxypropylene alkyl ether and lecithin derivatives.

These may be used either singly or in any combination thereof.

Other surfactants than nonionic surfactants, such as anionic surfactants, cationic surfactants and amphoteric surfactants, may also be used in the first liquid concentrate composition.

The content ratio of the surfactant is preferably 0.1 to 10% by mass, more preferably 0.5 to 8.0% by mass, particularly preferably 1.0 to 4.0% by mass, per 100% by mass of the first liquid concentrate composition.

If the content ratio of the surfactant is too high, the production cost will become high, and for human body applications, in particular, the composition may not give a favorable feeling when applied, as the surfactant adds a sticky feel. On the other hand, if the content ratio of the surfactant is too low, sufficient foam-forming ability may not be achieved, and the first liquid concentrate composition may not have sufficient emulsification stability.

Examples of higher alcohols, as an essential component of the first liquid concentrate composition, include lauryl alcohol, myristyl alcohol, cetyl alcohol, cetostearyl alcohol, arachyl alcohol, behenyl alcohol, oleyl alcohol, jojoba alcohol, stearyl alcohol, cholesterol, phytosterol, lanolin alcohol, octyldodecanol, hexyldecanol and isostearyl alcohol.

These may be used either singly or in any combination thereof.

Cetyl alcohol or cetostearyl alcohol, particularly cetyl alcohol, may preferably be used as higher alcohol in the first liquid concentrate composition.

The content ratio of the higher alcohol is preferably 0.1 to 10.0% by mass, more preferably 1.0 to 5.0% by mass, particularly preferably 2.0 to 4.0% by mass, per 100% by mass of the first liquid concentrate composition.

If the content ratio of the higher alcohol is too high, the viscosity of the first liquid concentrate composition will increase, because of which sufficient foam-forming ability may not be achieved. On the other hand, if the content ratio of the higher alcohol is too low, the viscosity of the first liquid concentrate composition will decrease, which may lead to dripping at the application site. Also, the first liquid concentrate composition may not have sufficient emulsification stability. Moreover, for human body applications, the composition may not give a favorable feeling when applied.

The first liquid concentrate composition may contain other optional components as required in addition to the essential components of the organic acid, water, surfactant and higher alcohol.

Examples of the optional components include esters, oil-based materials, polyhydric alcohols, waxes, film forming agents, other base conditioning agents (such as a moisturizer, a thickener and a pigment), medicinal agents and fragrance ingredients. Esters are preferable among these.

Esters may be used in the first liquid concentrate composition relating to the foam forming aerosol product of the present invention as a viscosity adjusting agent for the first liquid concentrate composition, for example, or, for human body applications in particular, as a moisturizer or an emollient ingredient for improving the feeling when used.

Examples of esters includes higher fatty acid esters including ethyl linoleate, isopropyl myristate, isopropyl palmitate, isopropyl isostearate, lanolin fatty acid isopropyl ester, lanolin acid hexyl ester, myristylmyristate, octyldodecyl myristate, cetyl lactate, ethyl oleate, decyl oleate, octyldodecyl oleate, cetyl octanoate, dioctyl succinate, glyceryl tricaprylate, glyceryl triisostearate, propylene glycol dicaprate, cetyl palmitate and glyceryl tricaprylate/caprate. These may be used either singly or in any combination thereof.

The content ratio of esters may differ depending on the purpose of use of the foam forming aerosol product, or the types and content ratios of other constituent components of the first liquid concentrate composition. However, the content ratio may preferably be 0.1 to 2.0% by mass, more preferably 0.2 to 1.0% by mass, particularly preferably 0.3 to 0.7% by mass, per 100% by mass of the first liquid concentrate composition.

If the content ratio of the esters is too high, sufficient foam-forming ability may not be achieved. For human body applications, in particular, a problem may arise as the ester adds a sticky feel, because of which the product may not give a favorable feeling when applied. On the other hand, if the content ratio of the esters is too low, the expected effects of esters in the foam forming aerosol product may not be fully exploited.

The first liquid concentrate composition composed of the essential and optional components as described above may preferably have a viscosity of 10 to 15000 mPa·s at a temperature of 20° C., more preferably 10 to 10000 mPa·s, particularly preferably 1000 to 5000 mPa·s.

If the viscosity of the first liquid concentrate composition is too high, the first liquid concentrate composition cannot be mixed sufficiently with the second liquid concentrate composition, because of which sufficient foam-forming ability may not be achieved. On the other hand, if the viscosity of the first liquid concentrate composition is too low, the product may tend to drip at the site of application.

The viscosity of the first liquid concentrate composition may preferably be within a range of ±20%, more preferably ±15%, of an average of the viscosities of the first liquid concentrate composition and the second liquid concentrate composition (hereinafter also referred to as "viscosity mean value"), in consideration of the relationship with the viscosity of the second liquid concentrate composition to be described later.

If the viscosity of the first liquid concentrate composition falls out of the range of the viscosity mean value noted above, i.e., if it is higher or lower than 20% of the viscosity mean value, there will be a large difference in the amount of the first liquid concentrate composition discharged from the first liquid concentrate filling space and that of the second liquid concentrate composition discharged from the second liquid concentrate filling space. As a result, the foam produced by the first and second liquid concentrate compositions mixed together may not exhibit sufficient foamability.

Second Liquid Concentrate Composition

The second liquid concentrate composition contains a hydrogen carbonate, water, a surfactant and a higher alcohol as essential components, the hydrogen carbonate being contained in a content ratio of 0.5 to 15.0% by mass.

Examples of hydrogen carbonates, as an essential component of the second liquid concentrate composition, include sodium hydrogen carbonate, calcium hydrogen carbonate and potassium hydrogen carbonate.

These may be used either singly or in any combination thereof.

As the hydrogen carbonate, sodium hydrogen carbonate may preferably be used from the viewpoints of the fact that it is highly safe and versatile and widely used in a variety of fields such as cosmetics, pharmaceuticals, domestic products, foods, and so on, as well as it is inexpensive.

The content ratio of the hydrogen carbonate needs to be 0.5 to 15.0% by mass, preferably 3.0 to 12.0% by mass, more preferably 5.0 to 11.0% by mass, per 100% by mass of the second liquid concentrate composition.

If the content ratio of the hydrogen carbonate is too high, the hydrogen carbonate may not be fully dissolved in the second liquid concentrate composition. The production cost will be higher, too. On the other hand, if the content ratio of the hydrogen carbonate is too low, sufficient foam-forming ability cannot be achieved.

Water as an essential component of the second liquid concentrate composition may be any of those given as examples of water that constitutes the first liquid concentrate composition.

The content ratio of water is preferably 70.0 to 99.0% by mass, more preferably 75.0 to 95.0% by mass, particularly preferably 80.0 to 90.0% by mass, per 100% by mass of the second liquid concentrate composition.

If the content ratio of water is too high, other ingredients may not be contained in a sufficient ratio in the second liquid concentrate composition. On the other hand, if the content ratio of water is too low, sufficient foam-forming ability may not be achieved, and the production cost may be increased.

As a surfactant, which is an essential component of the second liquid concentrate composition, a nonionic surfactant may preferably be used, as it is hardly affected by a hydrogen carbonate.

Nonionic surfactant as an essential component of the second liquid concentrate composition may be any of those given as examples of the nonionic surfactant that constitutes the first liquid concentrate composition.

These may be used either singly or in any combination thereof.

Other surfactants than nonionic surfactants, such as anionic surfactants, cationic surfactants and amphoteric surfactants, may also be used in the second liquid concentrate composition.

The content ratio of the surfactant is preferably 0.1 to 10% by mass, more preferably 0.5 to 8.0% by mass, particularly preferably 1.0 to 4.0% by mass, per 100% by mass of the second liquid concentrate composition.

If the content ratio of the surfactant is too high, the production cost will become high, and for human body applications, in particular, the composition may not give a favorable feeling when applied, as the surfactant adds a sticky feel. On the other hand, if the content ratio of the surfactant is too low, sufficient foam-forming ability may not be achieved, and the second liquid concentrate composition may not have sufficient emulsification stability.

Higher alcohol as an essential component of the second liquid concentrate composition may be any of those given as examples of the higher alcohol that constitutes the first liquid concentrate composition.

These may be used either singly or in any combination thereof.

Cetyl alcohol or cetostearyl alcohol, particularly cetyl alcohol, may preferably be used as higher alcohol in the second liquid concentrate composition.

The higher alcohol that constitutes the second liquid concentrate composition may be different from, or the same as, the higher alcohol that constitutes the first liquid concentrate composition, depending on the purpose of use of the foam forming aerosol product, or on the ease and cost of production.

The content ratio of the higher alcohol is preferably 0.1 to 10.0% by mass, more preferably 1.0 to 5.0% by mass, particularly preferably 2.0 to 4.0% by mass, per 100% by mass of the second liquid concentrate composition.

If the content ratio of the higher alcohol is too high, the viscosity of the second liquid concentrate composition will increase, because of which sufficient foam-forming ability may not be achieved. On the other hand, if the content ratio of the higher alcohol is too low, the viscosity of the second liquid concentrate composition will decrease, which may lead to dripping at the application site. Also, the second liquid concentrate composition may not have sufficient emulsification stability. Moreover, for human body applications, the composition may not give a favorable feeling when applied.

The second liquid concentrate composition may contain other optional components as required in addition to the essential components of the hydrogen carbonate, water, surfactant and higher alcohol. Optional components may be any of those given as examples of the optional components that constitute the first liquid concentrate composition, for example, among which esters are preferable.

The content ratio of esters may differ depending on the purpose of use of the foam forming aerosol product, or the types and content ratios of other constituent components of the second liquid concentrate composition. However, the content ratio may preferably be 0.1 to 2.0% by mass, more preferably 0.2 to 1.0% by mass, particularly preferably 0.3 to 0.7% by mass, per 100% by mass of the second liquid concentrate composition.

If the content ratio of the esters is too high, sufficient foam-forming ability may not be achieved, and for human body applications, in particular, a problem may arise as the ester adds a sticky feel, because of which the product may not give a favorable feeling when applied. On the other hand, if the content ratio of the esters is too low, the expected effects of esters in the foam forming aerosol product may not be fully exploited.

The second liquid concentrate composition composed of the essential and optional components as described above may preferably have a viscosity of 10 to 15000 mPa·s at a temperature of 20° C., more preferably 10 to 10000 mPa·s, particularly preferably 1000 to 5000 mPa·s.

If the viscosity of the second liquid concentrate composition is too high, the second liquid concentrate composition cannot be mixed sufficiently with the first liquid concentrate composition, because of which sufficient foam-forming ability may not be achieved. On the other hand, if the viscosity of the second liquid concentrate composition is too low, the product may tend to drip at the site of application.

The viscosity of the second liquid concentrate composition may preferably be within a range of ±20%, more preferably ±15%, of an average of the viscosities of the first liquid concentrate composition and the second liquid concentrate composition (viscosity mean value), in consideration of the relationship with the viscosity of the first liquid concentrate composition.

If the viscosity of the second liquid concentrate composition falls out of the range of the viscosity mean value noted above, i.e., if it is higher or lower than 20% of the viscosity mean value, there will be a large difference in the amount of the first liquid concentrate composition discharged from the first liquid concentrate filling space and that of the second liquid concentrate composition discharged from the second liquid concentrate filling space. As a result, the foam produced by the first and second liquid concentrate compositions mixed together may not exhibit sufficient foamability.

(Propellant)

A compressed gas is used as the propellant.

Examples of compressed gases include nitrous oxide gas, nitrogen gas, carbon dioxide and a mixture of these.

Nitrogen gas is preferable as the propellant of the first liquid concentrate composition.

The propellant may preferably be sealed in the double structure container at a pressure of 0.3 to 0.8 MPa at 25° C.

If the fill pressure of the propellant (product internal pressure) is too high or too low, the product may not be sprayed in a favorable manner in either case.

(Double Structure Container)

The double structure container that constitutes the foam forming aerosol product of the present invention includes a propellant filling space to be filled with a propellant, a first liquid concentrate filling space to be filled with a first liquid concentrate composition, and a second liquid concentrate filling space to be filled with a second liquid concentrate composition. The double structure container further includes a discharging mechanism for discharging the first and second liquid concentrate compositions simultaneously from the respective first and second liquid concentrate filling spaces.

The following four containers to be described below and shown in FIG. 1 to FIG. 6 are specific examples of the double structure container according to the present invention.

Figure 2:
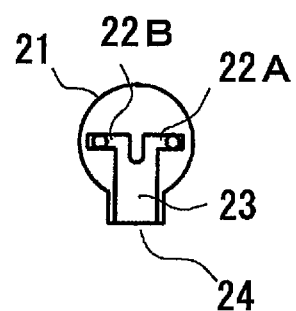
FIG. 2 is a cross-sectional view illustrating an A-A' section of FIG. 1.

FIG. 1 is a diagram illustrating one example of the structure of the double structure container used for the foam forming aerosol product of the present invention, and FIG. 2 is a cross-sectional view illustrating an A-A section of FIG. 1.

This double structure container 10 includes a pressure resistant container 11 made of metal and provided with an aerosol valve 12. Inside the pressure resistant container 11 are provided a first inner bag 15A that is made of aluminum laminated film, for example, and defines the first liquid concentrate filling space to be filled with the first liquid concentrate composition, and a second inner bag 15B that is made of aluminum laminated film, for example, and defines the second liquid concentrate filling space to be filled with the second liquid concentrate composition. A gap-space surrounded by these pressure resistant container 11, first inner bag 15A and second inner bag 15B form a propellant filling space to be filled with a propellant. The aerosol valve 12 is provided with a first stem 14A and a second stem 14B that have a stem passage inside and are arranged movable up and down inside a first housing 13A and a second housing 13B, respectively. A shared actuator 21 is provided to the upper ends of these first and second stems 14A and 14B.

In the illustrated example, reference symbol 16A denotes a dip tube that communicates with the stem passage in the first stem 14A at the lower end of the first housing 13A that forms the aerosol valve 12. The first dip tube 16A extends toward the bottom of the pressure resistant container 11 inside the first inner bag 15A. Reference symbol 16B denotes a dip tube that communicates with the stem passage in the second stem 14B at the lower end of the second housing 13B that forms the aerosol valve 12. The second dip tube 16B extends toward the bottom of the pressure resistant container 11 inside the second inner bag 15B.

In FIG. 1, the constituent elements disposed inside the pressure resistant container 11 and the actuator 21 are drawn with broken lines.

The shared actuator 21 is provided with a first actuator passage 22A that communicates with the stem passage of the first stem 14A, a second actuator passage 22B that communicates with the stem passage of the second stem 14B, and a mixing space 23 that communicates with these first and second actuator passages 22A and 22B at one end and forms a discharge port 24 at the other end.

The shared actuator 21 provided in this way with the first stem 14A associated with the first inner bag 15A that forms the first liquid concentrate filling space and the second stem 14B associated with the second inner bag 15B that forms the second liquid concentrate filling space constitutes the discharging mechanism for discharging the first liquid concentrate composition filled in the first inner bag 15A and the second liquid concentrate composition filled in the second inner bag 15B simultaneously from the first inner bag 15A and the second inner bag 15B, respectively.

In this double structure container 10 configured as described above, the first liquid concentrate composition is filled in the first inner bag 15A while the second liquid concentrate composition is filled in the second inner bag 15B in the pressure resistant container 11. Furthermore, the propellant filling space formed by the gap-space surrounded by the pressure resistant container 11, first bag 15A and second bag 15B is filled with a propellant, so that the inside of the pressure resistant container 11 is always pressurized by the propellant. When the actuator 21 is operated (depressed), the pressure of the propellant squeezes the first inner bag 15A and the second inner bag 15B, whereby the first and second liquid concentrate compositions are discharged simultaneously from the first and second inner bags 15A and 15B, and then from the discharge port 24 of the actuator 21 as a mixture.

More specifically, in the double structure container 10 holding the first and second liquid concentrate compositions and the propellant filled therein, when the actuator 21 is not operated, or not depressed, the first stem 14A and the second stem 14B are pushed upward to shut their stem passages from the inside of the pressure resistant container 11. When the actuator 21 is operated (depressed), the first stem 14A and the second stem 14B are pressed down, whereby their stem passages are simultaneously communicated with the inside of the pressure resistant container 11. The first liquid concentrate composition inside the first inner bag 15A and the second liquid concentrate composition inside the second inner bag 15B in the pressure resistant container 11 flow out through the fluid passages formed by the first dip tube 16A and the second dip tube 16B, respectively. The first and second liquid concentrate compositions thus flowing out simultaneously travel through the stem passages in the first stem 14A and the second stem 14B of the aerosol valve 12 and the first and second actuator passages 22A and 22B in the actuator 21, and reach the mixing space 23, where they are mixed to form a foam, which is then discharged from the discharge port 24 as a foamy discharge.

Figure 3:
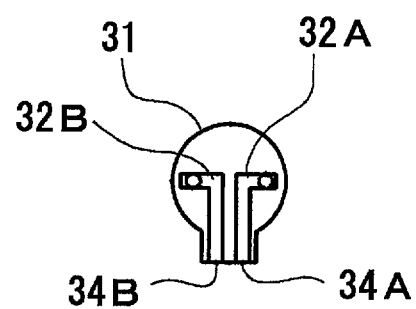
FIG. 3 is a diagram illustrating another example of the structure of the double structure container used for the foam forming aerosol product of the present invention.

FIG. 3 is a diagram illustrating another example of the structure of the double structure container used for the foam forming aerosol product of the present invention. More specifically, the drawing is a cross-sectional view for describing the structure of the actuator for the double structure container.

This double structure container is configured similarly to the double structure container 10 shown in FIG. 1 and FIG. 2 except that it has an actuator 31 instead of the actuator 21 of the double structure container 10 of FIG. 1 and FIG. 2. Specifically, the actuator 31 has two discharge ports (more specifically, a first discharge port 34A and a second discharge port 34B) and is configured to separately discharge the first and second liquid concentrate compositions from the respective discharge ports.

Namely, the double structure container associated with FIG. 3 includes the actuator 31, and a pressure resistant container that is configured similarly to the pressure resistant container 11 that constitutes the double structure container 10 shown in FIG. 1 and FIG. 2.

The actuator 31 is configured to include a first actuator passage 32A that is in communication with the stem passage of a first stem at one end and forms a first discharge port 34A at the other end, and a second actuator passage 32B that is in communication with the stem passage of a second stem at one end and forms a second discharge port 34B at the other end.

The actuator 31 is shared by both of the first and second stems and provided to the upper ends of the first and second stems, similarly to the actuator 21 of the double structure container 10 shown in FIG. 1 and FIG. 2.

In this double structure container configured as described above, when it is filled with first and second liquid concentrate compositions and a propellant, and when the actuator 31 is operated (depressed), the first and second liquid concentrate compositions are discharged simultaneously from the first and second inner bags inside the pressure resistant container, respectively. The first liquid concentrate composition is ejected from the first discharge port 34A through the stem passage in the first stem of the aerosol valve and the first actuator passage 32A of the actuator 31, while the second liquid concentrate composition is ejected from the second discharge port 34B through the stem passage in the second stem of the aerosol valve and the second actuator passage 32B of the actuator 31. The first and second liquid concentrate compositions discharged from the first and second discharge ports 34A and 34B respectively are then mixed, for example, with a finger, to form a foam, on the spot where they are applied.

Figure 4:
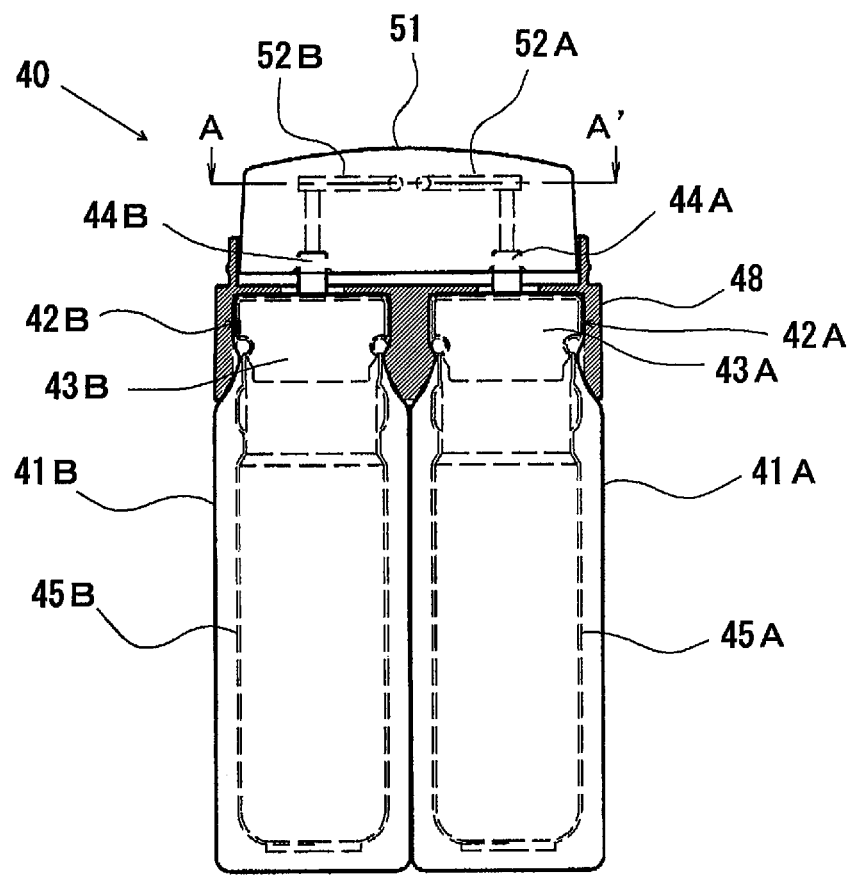
FIG. 4 is a diagram illustrating yet another example of the structure of the double structure container used for the foam forming aerosol product of the present invention.
Figure 5:
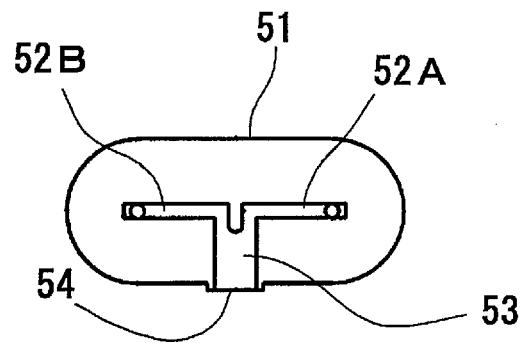
FIG. 5 is a cross-sectional view illustrating an A-A' section of FIG. 4.

FIG. 4 is a diagram illustrating yet another example of the structure of the double structure container used for the foam forming aerosol product of the present invention, and FIG. 5 is a cross-sectional view illustrating an A-A' section of FIG. 4.

This double structure container 40 is configured to have a first pressure resistant container 41A made of metal and provided with a first aerosol valve 42A, and a second pressure resistant container 41B made of metal and provided with a second aerosol valve 42B, with these containers being united with a container retainer 48.

Inside the first pressure resistant container 41A that constitutes the double structure container 40 are formed a first inner bag 45A that is made of polyethylene sheet, for example, and defines a first liquid concentrate filling space to be filled with a first liquid concentrate composition, and a propellant filling space to be filled with a propellant, which is formed by a gap-space surrounded by the first pressure resistant container 41A and the first inner bag 45A. The first aerosol valve 42A is provided with a first stem 44A having a stem passage inside and is arranged movable up and down inside a first housing 43A.

The second pressure resistant container 41B that constitutes the double structure container 40 is configured similarly to the first pressure resistant container 41A. More specifically, inside the second pressure resistant container 41B are formed a second inner bag 45B that is made of polyethylene sheet, for example, and defines a second liquid concentrate filling space to be filled with a second liquid concentrate composition, and a propellant filling space to be filled with a propellant, which is formed by a gap-space surrounded by the second pressure resistant container 41B and the second inner bag 45B. The second aerosol valve 42B is provided with a second stem 44B having a stem passage inside and is arranged movable up and down inside a second housing 43B.

In the illustrated example, the container retainer 48 has an outer appearance in the shape of an oval column. On one side (underside in FIG. 4) of the container retainer 48 are formed cavities having diameters that match those of the first and second housings 43A and 433 that form the first and second aerosol dispensing valves 42A and 42B, respectively. The first housing 43A and the second housing 43B are fitted in the respective cavities so that the first and second pressure resistant containers 41A and 41B are retained. The first stem 44A and the second stem 44B protrude from the first and second pressure resistant containers 41A and 41B fixed to the container retainer 48 through holes formed in the center of the cavities of the container retainer 48 with diameters that match those of the first and second stems 44A and 44B.

In FIG. 4, the constituent elements disposed inside the first pressure resistant container 41A, second pressure resistant container 41B and actuator 51 are drawn with broken lines.

A shared actuator 51 is provided to the upper ends of the first stem 44A of the first aerosol valve 42A and the second stem 44B of the second aerosol valve 42B.

The shared actuator 51 is provided with a first actuator passage 52A that is in communication with the stem passage of the first stem 44A, a second actuator passage 52B that is in communication with the stem passage of the second stem 44B, and a mixing space 53 that is in communication with these first and second actuator passages 52A and 52B at one end and forms a discharge port 54 at the other end.

The shared actuator provided in this way with the first stem 44A and the second stem 44B constitutes the discharging mechanism for discharging the first liquid concentrate composition filled in the first inner bag 45A and the second liquid concentrate composition filled in the second inner bag 45B simultaneously from the first inner bag 45A and the second inner bag 45B, respectively.

In this double structure container 40 configured as described above, the first liquid concentrate composition is filled in the first inner bag 45A in the first pressure resistant container 41A, and the propellant filling space formed by the gap-space surrounded by the pressure resistant container 41A and the first bag 45A is filled with a propellant, so that the inside of the first pressure resistant container 41A is always pressurized by the propellant. In the second pressure resistant container 41B, the second liquid concentrate composition is filled in the second inner bag 45B, and the propellant filling space formed by the gap-space surrounded by the second pressure resistant container 41B and the second bag 45B is filled with a propellant, so that the inside of the second pressure resistant container 41B is always pressurized by the propellant. When the actuator 51 is operated (depressed), the pressure of the propellant squeezes the first inner bag 45A and the second inner bag 45B, whereby the first and second liquid concentrate compositions are discharged simultaneously from the first and second inner bags 45A and 45B, and then from the discharge port 54 of the actuator 51 as a mixture.

More specifically, in the double structure container 40 holding the first and second liquid concentrate compositions and the propellant filled therein, when the actuator 51 is not operated, or not depressed, the first stem 44A and the second stem 44B are pushed upward to shut their stem passages from the inside of the first pressure resistant container 41A and of the second pressure resistant container 41B. When the actuator 51 is operated (depressed), the first stem 44A and the second stem 44B are pressed down, whereby their stem passages are simultaneously communicated with the inside of the first pressure resistant container 41A and of the second pressure resistant container 41B. As a result, the first liquid concentrate composition inside the first inner bag 45A in the first pressure resistant container 41A and the second liquid concentrate composition inside the second inner bag 45B in the second pressure resistant container 41B flow out simultaneously. The first and second liquid concentrate compositions thus flowing out simultaneously travel through the stem passages in the first stem 44A and the second stem 44B and the first and second actuator passages 52A and 52B in the actuator 51, and reach the mixing space 53, where they are mixed to form a foam, which is then discharged from the discharge port 54 as a foamy discharge.

Figure 6:
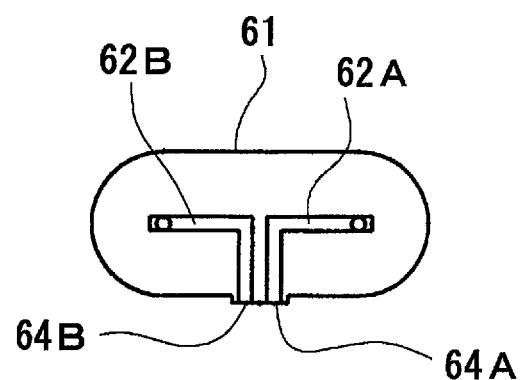
FIG. 6 is a diagram illustrating a further example of the structure of the double structure container used for the foam forming aerosol product of the present invention.

FIG. 6 is a diagram illustrating a further example of the structure of the double structure container used for the foam forming aerosol product of the present invention. More specifically, it is a cross-sectional view for explaining the structure of the actuator for the double structure container.

This double structure container is configured similarly to the double structure container 40 shown in FIG. 4 and FIG. 5 except that it has an actuator 61 instead of the actuator 51 of the double structure container 40 of FIG. 4 and FIG. 5. Specifically, the actuator 61 has two discharge ports (more specifically, a first discharge port 64A and a second discharge port 64B) and is configured to separately discharge the first and second liquid concentrate compositions from the respective discharge ports.

Namely, the double structure container associated with FIG. 6 includes the actuator 61, and a container body that is configured similarly to the container body that forms the double structure container 40 shown in FIG. 5 and FIG. 6 and includes the first pressure resistant container 41A, the second pressure resistant container 41, and the container retainer 48.

The actuator 61 is configured to include a first actuator passage 62A that is in communication with the stem passage of a first stem at one end and forms a first discharge port 64A at the other end, and a second actuator passage 62B that is in communication with the stem passage of a second stem at one end and forms a second discharge port 64B at the other end.

The actuator 61 is shared by both of the first and second stems and provided to the upper ends of the first and second stems, similarly to the actuator 51 of the double structure container 40 shown in FIG. 4 and FIG. 5.

In this double structure container configured as described above, when it is filled with first and second liquid concentrate compositions and a propellant, and when the actuator 61 is operated (depressed), the first and second liquid concentrate compositions are discharged simultaneously from the first and second inner bags inside the first and second pressure resistant containers, respectively. The first liquid concentrate composition is ejected from the first discharge port 64A through the stem passage in the first stem of the first aerosol valve and the first actuator passage 62A of the actuator 61. The second liquid concentrate composition is ejected from the second discharge port 64B through the stem passage in the second stem of the second aerosol valve and the second actuator passage 62B of the actuator 61. The first and second liquid concentrate compositions discharged from the first and second discharge ports 64A and 64B respectively are then mixed, for example, with a finger, to form a foam, on the spot where they are applied.

With the double structure container having the configuration described above, the first liquid concentrate composition filled in the first liquid concentrate filling space and the second liquid concentrate composition filled in the second liquid concentrate filling space can be discharged simultaneously by means of the discharging mechanism, and also, the amount of the first liquid concentrate composition discharged from the first liquid concentrate filling space and the amount of the second liquid concentrate composition discharged from the second liquid concentrate filling space can be adjusted to achieve an appropriate mass ratio in accordance with the relationship between the organic acid concentration of the first liquid concentrate composition and the hydrogen carbonate concentration of the second liquid concentrate composition or other factors.

In the foam forming aerosol product of the present invention, the mixture ratio of the first liquid concentrate composition discharged from the first liquid concentrate filling space and the second liquid concentrate composition discharged from the second liquid concentrate filling space (mass of the first liquid concentrate composition: mass of the second liquid concentrate composition) may preferably be 0.8:1.2 to 1.2:0.8.

That is, each of the amount of the first liquid concentrate composition discharged from the first liquid concentrate filling space and the amount of the second liquid concentrate composition discharged from the second liquid concentrate filling space may preferably be within a range of ±20% of an average of the discharge amounts of the first liquid concentrate composition and the second liquid concentrate composition.

The mixture ratio (mass of the first liquid concentrate composition: mass of the second liquid concentrate composition) may be made to fall within the range noted above by, for example, preparing the first liquid concentrate composition to have a viscosity of 10 to 15000 mPa·s at a temperature of 20° C., and the second liquid concentrate composition to have a viscosity of 10 to 15000 mPa·s at a temperature of 20° C., and further by preparing both liquid concentrate compositions to have a viscosity at the temperature of 20° C. that falls within the range of ±20% of a viscosity mean value.

If the mixture ratio (mass of the first liquid concentrate composition: mass of the second liquid concentrate composition) falls out of the range noted above, there will be a large difference in the amount of the first liquid concentrate composition discharged from the first liquid concentrate filling space and that of the second liquid concentrate composition discharged from the second liquid concentrate filling space. As a result, the foam produced by the first and second liquid concentrate compositions mixed together may not exhibit sufficient foamability.

The foam forming aerosol product of the present invention described above is produced by filling the first and second liquid concentrate filling spaces in the double structure container with a first liquid concentrate composition and a second liquid concentrate composition, respectively, and by filling the propellant filling space with a propellant.

The foam forming aerosol product of the present invention includes a double structure container having a discharging mechanism for simultaneously discharging contents filled in two liquid concentrate filling spaces. A first liquid concentrate composition containing an organic acid in a specific ratio is filled in one of the two liquid concentrate filling spaces, while a second liquid concentrate composition containing a hydrogen carbonate in a specific ratio is filled in the other liquid concentrate filling space. Accordingly, the first liquid concentrate composition and the second liquid concentrate composition can be discharged from the respective two liquid concentrate filling spaces of the double structure container in an appropriate amount at the same time. Therefore, the first liquid concentrate composition and the second liquid concentrate composition can always be mixed in a constant amount ratio, so that one liquid concentrate composition is never discharged excessively relative to the discharge amount of the other liquid concentrate composition. Accordingly, a simple operation of the discharging mechanism, more specifically, for example, pressing down an actuator once (one push), expels the first liquid concentrate composition and the second liquid concentrate composition, whereby a favorable foam is always readily formed by the carbon dioxide gas that is generated by the reaction between the organic acid and the hydrogen carbonate.

Since an incombustible compressed gas is used as the propellant of the first liquid concentrate composition and the second liquid concentrate composition, the product can be used highly safely irrespective of the environment in which it is used, and there is no risk of explosion hazards when disposing of the aerosol container. Moreover, as neither of the first liquid concentrate composition and the second liquid concentrate composition is exposed to the air outside the container, they can be maintained stable over a long term storage.

Accordingly, the foam forming aerosol product of the present invention can be used highly safely irrespective of the environment in which it is used, has excellent storage stability, and is capable of readily dispensing a favorable foam.

With the foam forming aerosol product of the present invention, if the discharging mechanism that constitutes the double structure container includes a mixing space for mixing the first liquid concentrate composition discharged from the first liquid concentrate filling space and the second liquid concentrate composition discharged from the second liquid concentrate filling space, more specifically, if the actuator is formed with a mixing space as shown in FIG. 2 and FIG. 5, for example, the product can deliver a foamy discharge. Therefore, it can be applied in a given site easily as there is no need to mix the first liquid concentrate composition and the second liquid concentrate composition.

If the foam forming aerosol product of the product has such a double structure container as shown in FIG. 3 and FIG. 6, for example, which includes a discharging mechanism having an actuator that discharges the first liquid concentrate composition discharged from the first liquid concentrate filling space and the second liquid concentrate composition discharged from the second liquid concentrate filling space from separate discharge ports, it is necessary to mix the first and second liquid concentrate compositions at the site of application to form a foam. On the other hand, it can be enjoyable to watch as the foam develops or changes its form.

The foam forming aerosol product of the present invention can be used, for example, for the human body and for a variety of other purposes. Since the foam is formed by carbon dioxide gas, which is expected to induce an increase in blood flow, the aerosol product may preferably be used particularly for the human body.

More specifically, the aerosol product may be used for dispensing hair styling agent, hair wax, hair treatment, hair coloring agent, shampoo, conditioner, hair growth agent, massaging agent, facial soap, cleanser, shaving agent, makeup base, skin protector, moisturizer, whitening agent, sunscreen agent, hair remover, hand soap, body soap, and so on.

EXAMPLES

While examples of the present invention will hereinafter be described, the present invention should not be limited by these examples.

Examples 1 to 12 and Comparative Example 1

(Preparation of First Liquid Concentrate Composition)

First, a cream base "Emacol HD2146" (manufactured by San-Ei Kagaku Co., Ltd.) was heated to a temperature range of 80 to 85° C. to obtain an oleaginous solution (oil phase). Meanwhile, purified water, polyoxyethylene lauryl ether "BL-9EX" (manufactured by Nikko Chemicals Co., Ltd.) as a surfactant, and other materials of the first liquid concentrate composition, as required, were mixed and heated to a temperature range of 80 to 85° C. to obtain an aqueous solution (water phase).

Next, an emulsion was prepared by slowly adding the thus obtained aqueous solution (water phase) to the thus obtained oleaginous solution (oil phase) that was being stirred at a stirring (rotation) speed of 600 rpm with the use of a propeller stirrer. After the thus obtained emulsion was cooled down to 30° C. or lower, a first liquid concentrate composition having the composition shown in Table 1 and Table 2 was prepared by adding an organic acid and stirring at a stirring speed of 600 rpm.

Note that the cream base "Emacol HD2146" (manufactured by San-Ei Kagaku Co., Ltd.) contains cetyl alcohol (60% by mass), isopropyl palmitate (8% by mass), sodium cetyl sulfate (7% by mass), beeswax (5% by mass), ceteth-6 (5% by mass), ceteth-30 (5% by mass), ceteth-40 (5% by mass) and water (5% by mass).

(Preparation of Second Liquid Concentrate Composition)

First, a cream base "Emacol HD2146" (manufactured by San-Ei Kagaku Co., Ltd.) was heated to a temperature range of 80 to 85° C. to obtain an oleaginous solution (oil phase). Meanwhile, purified water, polyoxyethylene lauryl ether "BL-9EX" (manufactured by Nikko Chemicals Co., Ltd.) as a surfactant, and other materials of the second liquid concentrate composition, as required, were mixed and heated to a temperature range of 80 to 85° C. to obtain an aqueous solution (water phase).

Next, an emulsion was prepared by slowly adding the thus obtained aqueous solution (water phase) to the thus obtained oleaginous solution (oil phase) that was being stirred at a stirring (rotation) speed of 600 rpm with the use of a propeller stirrer. After the thus obtained emulsion was cooled down to 30° C. or lower, a second liquid concentrate composition having the composition shown in Table 1 and Table 2 was prepared by adding a hydrogen carbonate and stirring at a stirring speed of 600 rpm.

(Fabrication of Aerosol Spray Product)

The aerosol spray product was fabricated as follows: A double structure container having the configuration shown in FIG. 1 and FIG. 2 was prepared, and the first liquid concentrate filling space (first inner bag) of the double structure container was filled with the first liquid concentrate composition, while the second liquid concentrate filling space (second inner bag) was filled with the second liquid concentrate composition. The propellant filling space was filled with nitrogen gas as a propellant to achieve a product internal pressure of 0.7 MPa at 25° C. in the double structure container.

Comparative Example 2

An aerosol product was fabricated for comparative purposes by the same method as in Example 1, except that an emulsion obtained through preparation of the first liquid concentrate composition according to Example 1 was filled in the first liquid concentrate filling space (first inner bag) of the double structure container instead of the first liquid concentrate composition, and an emulsion obtained through preparation of the second liquid concentrate composition according to Example 1 was filled in the second liquid concentrate filling space (second inner bag) instead of the second liquid concentrate composition in Example 1.

<Evaluation Test>

The aerosol products fabricated as Examples 1 to 12 and Comparative Examples 1 and 2 were evaluated by the following method in terms of the foamability of the discharge. The results are shown in Table 1 and Table 2.

(Foamability of the Discharge)

5 g of the content of each aerosol product was sprayed into a 50 ml glass beaker. After stirring the discharge in the beaker by slowly rotating a glass rod ten times, the volume of the discharge in the beaker was measured. The composition is evaluated as "A" for having a very good foamability, if its volume is not less than 40 ml. The composition is evaluated as "B" for having a good foamability, if its volume is not less than 20 ml and less than 40 ml. The composition is evaluated as "C" for having insufficient foamability, if its volume is less than 20 ml.

TABLE 1

|  |  |  | Example 1 | | Example 2 | | Example 3 | | Example 4 |
| --- | --- | --- | --- | --- | --- | --- | --- | --- | --- |
|  |  |  | First composition | Second composition | First composition | Second composition | First composition | Second composition | First composition |
| Composition | Organic acid (mass %) | Citric acid | 8.32 | — | 6.40 | — | — | — | — |
|  |  | Lactic acid | — | — | — | — | 6.40 | — | — |
|  |  | Fumaric acid | — | — | — | — | — | — | 6.40 |
|  | Hydrogen carbonate (mass %) | Sodium hydrogen carbonate | — | 10.92 | — | 8.40 | — | 8.40 | — |
|  | Water (mass %) | Purified water | 84.93 | 82.33 | 87.80 | 85.80 | 86.85 | 84.85 | 86.85 |
|  | Nonionic surfactant (mass %) | Polyoxyethylene lauryl ether | 2.00 | 2.00 | 2.00 | 2.00 | 2.00 | 2.00 | 2.00 |
|  |  | Polyoxyethylene alkyl ether(1) | 0.25 | 0.25 | 0.20 | 0.20 | 0.25 | 0.25 | 0.25 |
|  |  | Polyoxyethylene alkyl ether(2) | 0.25 | 0.25 | 0.20 | 0.20 | 0.25 | 0.25 | 0.25 |
|  |  | Polyoxyethylene alkyl ether(3) | 0.25 | 0.25 | 0.20 | 0.20 | 0.25 | 0.25 | 0.25 |
|  | Anionic surfactant (mass %) | Sodium cetyl sulfate | 0.35 | 0.35 | 0.28 | 0.28 | 0.35 | 0.35 | 0.35 |
|  | Higher alcohol (mass %) | Cetyl alcohol | 3.00 | 3.00 | 2.40 | 2.40 | 3.00 | 3.00 | 3.00 |
|  | Polyhydric alcohol (mass %) | Glycerin | — | — | — | — | — | — | — |
|  |  | 1,3-butylene glycol | — | — | — | — | — | — | — |
|  | Ester (mass %) | Isopropyl palmitate | 0.40 | 0.40 | 0.32 | 0.32 | 0.40 | 0.40 | 0.40 |
|  | Wax (mass %) | Beeswax | 0.25 | 0.25 | 0.20 | 0.20 | 0.25 | 0.25 | 0.25 |
|  | Film forming agent (mass %) | Methacryloyl ethyl betaine/acrylate copolymer | — | — | — | — | — | — | — |
|  | Thickener (mass %) | Stearoxy hydroxypropyl methylcellulose | — | — | — | — | — | — | — |
|  | Medical agent (mass %) | Tranexamic acid | — | — | — | — | — | — | — |
|  | Total (mass %) |  | 100.00 | 100.00 | 100.00 | 100.00 | 100.00 | 100.00 | 100.00 |
|  | Liquid concentrate viscosity (mPa · s) |  | 3100 | 3450 | 1550 | 1720 | 3100 | 3400 | 3150 |
| Evaluation test | Foamability of discharge | Measurement | 60 ml or more | | 60 ml or more | | 60 ml or more | | 60 ml or more |
|  |  | Evaluation | A | | A | | A | | A |

|  |  |  | Example 4 | Example 5 | | Example 6 | | Example 7 | |
| --- | --- | --- | --- | --- | --- | --- | --- | --- | --- |
|  |  |  | Second composition | First composition | Second composition | First composition | Second composition | First composition | Second composition |
| Composition | Organic acid (mass %) | Citric acid | — | 6.40 | — | 6.40 | — | 6.40 | — |
|  |  | Lactic acid | — | — | — | — | — | — | — |
|  |  | Fumaric acid | — | — | — | — | — | — | — |
|  | Hydrogen carbonate (mass %) | Sodium hydrogen carbonate | 8.40 | — | 8.40 | — | 8.40 | — | 8.40 |
|  | Water (mass %) | Purified water | 84.85 | 76.85 | 74.85 | 76.85 | 74.85 | 82.75 | 80.75 |
|  | Nonionic surfactant (mass %) | Polyoxyethylene lauryl ether | 2.00 | 2.00 | 2.00 | 2.00 | 2.00 | 2.00 | 2.00 |
|  |  | Polyoxyethylene alkyl ether(1) | 0.25 | 0.25 | 0.25 | 0.25 | 0.25 | 0.25 | 0.25 |

TABLE 1-continued

|  |  |  |  |  |  |  |  |  |
|---|---|---|---|---|---|---|---|---|
|  | Polyoxyethylene alkyl ether(2) | 0.25 | 0.25 | 0.25 | 0.25 | 0.25 | 0.25 | 0.25 |
|  | Polyoxyethylene alkyl ether(3) | 0.25 | 0.25 | 0.25 | 0.25 | 0.25 | 0.25 | 0.25 |
| Anionic surfactant (mass %) | Sodium cetyl sulfate | 0.35 | 0.35 | 0.35 | 0.35 | 0.35 | 0.35 | 0.35 |
| Higher alcohol (mass %) | Cetyl alcohol | 3.00 | 3.00 | 3.00 | 3.00 | 3.00 | 3.00 | 3.00 |
| Polyhydric alcohol (mass %) | Glycerin | — | 10.00 | 10.00 | — | — | 3.00 | 3.00 |
|  | 1,3-butylene glycol | — | — | — | 5.00 | 5.00 | — | — |
| Ester (mass %) | Isopropyl palmitate | 0.40 | 0.40 | 0.40 | 0.40 | 0.40 | 0.40 | 0.40 |
| Wax (mass %) | Beeswax | 0.25 | 0.25 | 0.25 | 0.25 | 0.25 | 0.25 | 0.25 |
| Film forming agent (mass %) | Methacryloyl ethyl betaine/ acrylate copolymer | — | — | — | 5.00 | 5.00 | — | — |
| Thickener (mass %) | Stearoxy hydroxypropyl methylcellulose | — | — | — | — | — | 0.10 | 0.10 |
| Medical agent (mass %) | Tranexamic acid | — | — | — | — | — | 1.00 | 1.00 |
|  | Total (mass %) | 100.00 | 100.00 | 100.00 | 100.00 | 100.00 | 100.00 | 100.00 |
|  | Liquid concentrate viscosity (mPa·s) | 3430 | 3300 | 3500 | 3150 | 3430 | 4400 | 4700 |
| Evaluation test | Foamability of discharge | Measurement | 60 ml or more | | 60 ml or more | | 60 ml or more | | 60 ml or more |
|  |  | Evaluation | A | | A | | A | | A |

TABLE 2

|  |  |  | Example 8 | | Example 9 | | Example 10 | | Example 11 |
|---|---|---|---|---|---|---|---|---|---|
|  |  |  | First composition | Second composition | First composition | Second composition | First composition | Second composition | First composition |
| Composition | Organic acid (mass %) | Citric acid | 8.32 | — | 2.56 | — | 1.28 | — | 8.32 |
|  | Hydrogen carbonate (mass %) | Sodium hydrogen carbonate | — | 10.92 | — | 3.36 | — | 1.64 | — |
|  | Water (mass %) | Purified water | 86.83 | 84.23 | 90.69 | 89.89 | 91.97 | 91.61 | 83.03 |
|  | Nonionic surfactant (mass %) | Polyoxyethylene lauryl ether | 2.00 | 2.00 | 2.00 | 2.00 | 2.00 | 2.00 | 2.00 |
|  |  | Polyoxyethylene alkyl ether (1) | 0.15 | 0.15 | 0.25 | 0.25 | 0.25 | 0.25 | 0.35 |
|  |  | Polyoxyethylene alkyl ether (2) | 0.15 | 0.15 | 0.25 | 0.25 | 0.25 | 0.25 | 0.35 |
|  |  | Polyoxyethylene alkyl ether (3) | 0.15 | 0.15 | 0.25 | 0.25 | 0.25 | 0.25 | 0.35 |
|  | Anionic surfactant (mass %) | Sodium cetyl sulfate | 0.21 | 0.21 | 0.35 | 0.35 | 0.35 | 0.35 | 0.49 |
|  | Higher alcohol (mass %) | Cetyl alcohol | 1.80 | 1.80 | 3.00 | 3.00 | 3.00 | 3.00 | 4.20 |
|  | Ester (mass %) | Isopropyl palmitate | 0.24 | 0.24 | 0.40 | 0.40 | 0.40 | 0.40 | 0.56 |
|  | Wax (mass %) | Beeswax | 0.15 | 0.15 | 0.25 | 0.25 | 0.25 | 0.25 | 0.35 |
|  |  | Total (mass %) | 100.00 | 100.00 | 100.00 | 100.00 | 100.00 | 100.00 | 100.00 |
|  |  | Liquid concentrate viscosity (mPa·s) | 615 | 680 | 3230 | 3380 | 3270 | 3350 | 6350 |
| Evaluation test | Foamability of discharge | Measurement | 60 ml or more | | 35 ml | | 25 ml | | 50 ml |
|  |  | Evaluation | A | | B | | B | | A |

TABLE 2-continued

|  |  |  | Example 11 | Example 12 | | Comparative Example 1 | | Comparative Example 2 | |
|---|---|---|---|---|---|---|---|---|---|
|  |  |  | Second composition | First composition | Second composition | First composition | Second composition | First composition | Second composition |
| Composition | Organic acid (mass %) | Citric acid | — | 8.32 | — | 0.32 | — | — | — |
|  | Hydrogen carbonate (mass %) | Sodium hydrogen carbonate | 10.92 | — | 10.92 | — | 0.42 | — | — |
|  | Water (mass %) | Purified water | 80.43 | 81.13 | 78.53 | 92.93 | 92.83 | 93.25 | 93.25 |
|  | Nonionic surfactant (mass %) | Polyoxyethylene lauryl ether | 2.00 | 2.00 | 2.00 | 2.00 | 2.00 | 2.00 | 2.00 |
|  |  | Polyoxyethylene alkyl ether (1) | 0.35 | 0.45 | 0.45 | 0.25 | 0.25 | 0.25 | 0.25 |
|  |  | Polyoxyethylene alkyl ether (2) | 0.35 | 0.45 | 0.45 | 0.25 | 0.25 | 0.25 | 0.25 |
|  |  | Polyoxyethylene alkyl ether (3) | 0.35 | 0.45 | 0.45 | 0.25 | 0.25 | 0.25 | 0.25 |
|  | Anionic surfactant (mass %) | Sodium cetyl sulfate | 0.49 | 0.63 | 0.63 | 0.35 | 0.35 | 0.35 | 0.35 |
|  | Higher alcohol (mass %) | Cetyl alcohol | 4.20 | 5.40 | 5.40 | 3.00 | 3.00 | 3.00 | 3.00 |
|  | Ester (mass %) | Isopropyl palmitate | 0.56 | 0.72 | 0.72 | 0.40 | 0.40 | 0.40 | 0.40 |
|  | Wax (mass %) | Beeswax | 0.35 | 0.45 | 0.45 | 0.25 | 0.25 | 0.25 | 0.25 |
|  |  | Total (mass %) | 100.00 | 100.00 | 100.00 | 100.00 | 100.00 | 100.00 | 100.00 |
|  |  | Liquid concentrate viscosity (mPa·s) | 6700 | 12300 | 13800 | 3290 | 3300 | 3300 | 3300 |
| Evaluation test | Foamability of discharge | Measurement | 50 ml | 20 ml | | 12 ml | | 10 ml | |
|  |  | Evaluation | A | B | | C | | C | |

In Table 1 and Table 2, "not less than 60 ml" in the cells of the row that indicates the measurements of the "foamability of the discharge" in the evaluation test means that the foam spilled over the top of the beaker.

In the tables, the "first composition" indicates the first liquid concentrate composition, the "second composition" indicates the second liquid concentrate composition. "Citric acid" is one that is manufactured by Kozakai Pharmaceutical Co., Ltd., "lactic acid" is one that is manufactured by Kanto Chemical Co., Inc., "fumaric acid" is one that is manufactured by Nippon Shokubai Co., Ltd., "sodium hydrogen carbonate" is one that is manufactured by Kozakai Pharmaceutical Co., Ltd., "polyoxyethylene lauryl ether" is "BL-9EX" (manufactured by Nikko Chemicals Co., Ltd.), "polyoxyethylene alkyl ether (1)" is "ceteth-6," "polyoxyethylene alkyl ether (2)" is "ceteth-30," "polyoxyethylene alkyl ether (3)" is "ceteth-40," "glycerin" is one that is manufactured by Kao Corporation and "1,3-butylene glycol" is one that is manufactured by Kyowa Hakko Chemical Co., Ltd.

As is seen from the results shown in Table 1, it was confirmed that the aerosol products of Examples 1 to 12 could readily form a favorable foam.

The aerosol products of Examples 1 to 12 had a first liquid concentrate composition and a second liquid concentrate composition with a viscosity within the range of 10 to 15000 mPa·s at a temperature of 25° C., with the viscosities also being within the range of ±20% of the average of the viscosities of the first and second liquid concentrate compositions. Accordingly, it was also confirmed that the mixture ratio of the first and second liquid concentrate compositions (mass of the first liquid concentrate composition: mass of the second liquid concentrate composition) of the discharge fell within the range of 0.8:1.2 to 1.2:0.8, and that the product exhibited a high foam-forming ability (foamability of the discharge).

On the other hand, in the aerosol product of Comparative Example 1 the content ratio of the organic acid in the first liquid concentrate composition and that of the hydrogen carbonate in the second liquid concentrate composition were both too low. Accordingly, the aerosol product could not form a good foam because of a poor foam-forming ability (foamability of the discharge) due to an insufficient amount of generated carbon dioxide gas.

The aerosol product of Comparative Example 2 did not form a foam because the two types of liquid concentrate compositions did not contain an organic acid and a hydrogen carbonate, respectively, and no carbon dioxide gas was generated when the liquid concentrate compositions were mixed.

It was also confirmed that the aerosol products of Examples 1 to 12 could still form a favorable foam even after they were stored for a long period of a month under an environment with a temperature of 45° C.

REFERENCE SIGNS LIST

10 Double structure container
11 Pressure resistant container
12 Aerosol valve
13A First housing
13B Second housing
14A First stem
14B Second stem
15A First inner bag 15B Second inner bag
16A First dip tube
16B Second dip tube
21 Actuator
22A First actuator passage
22B Second actuator passage
23 Mixing space
24 Discharge port
31 Actuator
32A First actuator passage
32B Second actuator passage
34A First discharge port
34B Second discharge port
40 Double structure container
41A First pressure resistant container
41B Second pressure resistant container
42A First aerosol valve
42B Second aerosol valve
43A First housing
43B Second housing
44A First stem
44B Second stem
45A First inner bag
45B Second inner bag
48 Container retainer
51 Actuator
52A First actuator passage
52B Second actuator passage
53 Mixing space
54 Discharge port
61 Actuator
62A First actuator passage
62B Second actuator passage
64A First discharge port
64B Second discharge port

The invention claimed is:

1. A foam forming aerosol dispenser comprising:
(a) a double structure container having a propellant filling space, the propellant filling space containing a compressed gas propellant;
(b) a first liquid concentrate filling space comprising contents containing a first liquid concentrate composition comprising an organic acid being in an amount of 0.5 to 15.0% by mass per 100% by mass of the first liquid concentrate composition, water, a surfactant, and at least one first alcohol selected from the group consisting of lauryl alcohol, myristyl alcohol, cetyl alcohol, cetostearyl alcohol, arachyl alcohol, behenyl alcohol, oleyl alcohol, jojoba alcohol, stearyl alcohol, cholesterol, phytosterol, lanolin alcohol, octyldodecanol, hexyldecanol and isostearyl alcohol, said at least one first alcohol being in an amount of 0.1 to 10.0% by mass per 100% by mass of the first liquid concentrate composition, the first liquid concentrate composition having a viscosity of 615 to 15000 mPa·s at a temperature of 20° C.;
(c) a second liquid concentrate filling space comprising contents containing a second liquid concentrate composition containing a hydrogen carbonate being in an amount of 0.5 to 15.0% by mass per 100% by mass of the second liquid concentrate composition, water, a surfactant, and at least one second alcohol selected from the group consisting of lauryl alcohol, myristyl alcohol, cetyl alcohol, cetostearyl alcohol, arachyl alcohol, behenyl alcohol, oleyl alcohol, jojoba alcohol, stearyl alcohol, cholesterol, phytosterol, lanolin alcohol, octyldodecanol, hexyldecanol and isostearyl alcohol, said at least one second alcohol being in an amount of 0.1 to 10.0% by mass per 100% by mass of the second liquid concentrate composition, the second liquid concentrate composition having a viscosity of 680 to 15000 mPa·s at a temperature of 20° C.; and
(d) a shared actuator for simultaneously discharging the contents contained in the first liquid concentrate filling space and the contents contained in the second liquid concentrate filling space,
the shared actuator being operable to discharge the first liquid concentrate composition from the first liquid concentrate filling space and to discharge the second liquid concentrate composition from the second liquid concentrate filling space so as to mix the first liquid concentrate composition with the second liquid concentrated composition to form a foam;
wherein each of the viscosity of the first liquid concentrate composition and the viscosity of the second liquid concentrate composition falls within a range of ±20% of an average of the viscosities of the first liquid concentrate composition and the second liquid concentrate composition.

2. The foam forming aerosol dispenser according to claim 1, wherein a ratio of the mass of the first liquid concentrate composition discharged from the first liquid concentrate filling space and the mass of the second liquid concentrate composition discharged from the second liquid concentrate filling space is 0.8:1.2 to 1.2:0.8.

3. The foam forming aerosol dispenser according to claim 1, wherein the shared actuator includes a mixing space for mixing the first liquid concentrate composition discharged from the first liquid concentrate filling space and the second liquid concentrate composition discharged from the second liquid concentrate filling space.

4. The foam forming aerosol dispenser according to claim 1, wherein the foam produced by the foam forming aerosol dispenser is compatible for application to a human body.

5. The foam forming aerosol dispenser according to claim 2, wherein the shared actuator includes a mixing space for mixing the first liquid concentrate composition discharged from the first liquid concentrate filling space and the second liquid concentrate composition discharged from the second liquid concentrate filling space.

6. The foam forming aerosol dispenser according to claim 1, wherein the surfactant in the first liquid concentrate composition is in an amount of 0.1 to 10.0% by mass per 100% by mass of the first liquid concentrate composition, and the surfactant in the second liquid concentrate composition is in an amount of 0.1 to 10.0% by mass per 100% by mass of the second liquid concentrate composition.

7. The foam foaming aerosol dispenser according to claim 1, wherein the first liquid concentrate composition further contains a higher fatty acid ester in an amount of 0.1 to 2.0% by mass per 100% by mass of the first liquid concentrate composition; and the second liquid concentrate composition further contains a higher fatty acid ester in an amount of 0.1 to 2.0% by mass per 100% by mass of the second liquid concentrate composition.

* * * * *